United States Patent
Leighton

(10) Patent No.: US 11,224,585 B2
(45) Date of Patent: Jan. 18, 2022

(54) COMPOSITIONS CONTAINING OMEGA-3 OIL AND USES THEREOF

(71) Applicant: Maine Natural Health Company, Inc., Warren, ME (US)

(72) Inventor: Harry J. Leighton, Rockport, ME (US)

(73) Assignee: Maine Natural Health Company, Inc., Warren, ME (US)

( * ) Notice: Subject to any disclaimer, the term of this patent is extended or adjusted under 35 U.S.C. 154(b) by 0 days.

(21) Appl. No.: 16/536,125

(22) Filed: Aug. 8, 2019

(65) Prior Publication Data
US 2019/0358191 A1 Nov. 28, 2019

Related U.S. Application Data

(63) Continuation of application No. 15/687,005, filed on Aug. 25, 2017, now abandoned, which is a continuation of application No. 14/706,506, filed on May 7, 2015, now abandoned, which is a continuation of application No. 13/822,517, filed as application No. PCT/US2011/051698 on Sep. 15, 2011, now abandoned.

(60) Provisional application No. 61/383,972, filed on Sep. 17, 2010.

(51) Int. Cl.
| | |
|---|---|
| A61K 31/23 | (2006.01) |
| A61K 31/192 | (2006.01) |
| A61K 31/20 | (2006.01) |
| A61K 31/355 | (2006.01) |
| A61K 31/726 | (2006.01) |
| A61K 45/06 | (2006.01) |
| A61K 31/202 | (2006.01) |
| A61K 31/7008 | (2006.01) |

(52) U.S. Cl.
CPC .......... *A61K 31/23* (2013.01); *A61K 31/192* (2013.01); *A61K 31/20* (2013.01); *A61K 31/202* (2013.01); *A61K 31/355* (2013.01); *A61K 31/7008* (2013.01); *A61K 31/726* (2013.01); *A61K 45/06* (2013.01)

(58) Field of Classification Search
CPC .... A61K 31/23; A61K 45/06; A61K 31/7008; A61K 31/192; A61K 31/20; A61K 31/726; A61K 31/355; A61K 31/202
USPC .......................................................... 514/62
See application file for complete search history.

(56) References Cited

U.S. PATENT DOCUMENTS

| | | |
|---|---|---|
| 5,130,242 A | 7/1992 | Barclay |
| 5,780,039 A | 7/1998 | Greenberg et al. |
| 6,121,470 A | 9/2000 | Takahashi et al. |
| 6,284,268 B1 | 9/2001 | Mishra et al. |
| 7,741,374 B1 | 6/2010 | Arnold et al. |
| 9,415,035 B2 | 8/2016 | Leighton |
| 2002/0044961 A1 | 4/2002 | Kirschner et al. |
| 2003/0104048 A1 | 6/2003 | Patel et al. |
| 2003/0161918 A1 | 8/2003 | Kendrick et al. |
| 2004/0052837 A1 | 3/2004 | Stillwell et al. |
| 2005/0113449 A1 | 5/2005 | Renshaw |
| 2005/0184275 A1 | 8/2005 | Mora-Gutierrez et al. |
| 2005/0187204 A1 | 8/2005 | Kondo et al. |
| 2006/0088574 A1 | 4/2006 | Manning et al. |
| 2006/0211749 A1 | 9/2006 | Bobotas et al. |
| 2007/0104779 A1 | 5/2007 | Rongen et al. |
| 2007/0141138 A1 | 6/2007 | Feuerstein et al. |
| 2007/0253941 A1 | 11/2007 | Naidu et al. |
| 2007/0269507 A1 | 11/2007 | Sachetto et al. |
| 2008/0085320 A1 | 4/2008 | Dror et al. |
| 2008/0268036 A1 | 10/2008 | Guy et al. |
| 2009/0099261 A1 | 4/2009 | Bell et al. |
| 2009/0149533 A1 | 6/2009 | Almarsson et al. |
| 2009/0186096 A1 | 7/2009 | Kritzman et al. |
| 2009/0215897 A1 | 8/2009 | Beermann et al. |
| 2009/0297665 A1 | 12/2009 | Bromley |
| 2010/0021555 A1 | 1/2010 | Geiringer et al. |
| 2010/0166918 A1 | 7/2010 | Miller |
| 2010/0173876 A1 | 7/2010 | Lichtenberger et al. |
| 2010/0197628 A1 | 8/2010 | Renshaw et al. |

FOREIGN PATENT DOCUMENTS

WO  WO 2008/147562  * 12/2008

OTHER PUBLICATIONS

Bloomer et al., "Effect of eicosapentaenoic and docosahexaenoic acid on resting and exercise-induced inflammatory and oxidative stress biomarkers: a randomized, placebo controlled, cross-over study," *Lipids in Health and Disease*, 8(36): 1-12 (2009).
Bozin et al., "Antimicrobial and antioxidant properties of rosemary and sage (*Rosmarinus officinalis* L. and *Salvia officinalis* L., Lamiaceae) essential oils," J Agric Food Chem. 55(19):7879-85 (2007).
Denomega Nutritional Oils Certificate of Analysis, dated Dec. 4, 2008 (2 pages).
Fearon et al., "Double-blind, placebo-controlled, randomized study of eicosapentaenoic acid diester in patients with cancer cachexia," *Journal of Clinical Oncology*, 24(21): 3401-3407 (2008).
International Preliminary Report on Patentability for International Application No. PCT/US2011/051698, dated Mar. 28, 2013.
International Preliminary Report on Patentability for International Application No. PCT/US2011/051734, dated Mar. 28, 2013.

(Continued)

*Primary Examiner* — Yih-Horng Shiao
(74) *Attorney, Agent, or Firm* — Clark & Elbing LLP

(57) ABSTRACT

The invention provides pharmaceutical compositions containing omega-3 oil and a non-hydrophilic co-solvent that have an increased absorption rate. The pharmaceutical compositions may further contain one or more pharmaceutical organic molecules. The invention further provides kits containing these pharmaceutical compositions, methods for formulating pharmaceutical compositions containing omega-3 oil, and methods for decreasing the likelihood of developing cardiovascular disease, decreasing triglyceride or LDL cholesterol levels, decreasing pain or inflammation, treating diabetes, chronic pulmonary diseases, or irritable bowel syndrome, decreasing symptoms of an autoimmune disease or allergic conditions.

29 Claims, No Drawings

(56) References Cited

OTHER PUBLICATIONS

International Search Report for International Application No. PCT/US2011/051698, dated Feb. 3, 2012 (3 pages).
International Search Report for International Application No. PCT/US2011/051734, dated Mar. 14, 2012 (3 pages).
Maine Natural Health, "OmegaMaine Omega-3 Liquid Oil in Five All Natural Flavors," <http://www.mainenaturalhealth.com/omega3.php>, retrieved Oct. 30, 2014 (2 pages).
Ratanabanangkoon et al., "A high-throughput approach towards a novel formulation of fenofibrate in omega-3 oil," Eur J Pharm Sci. 33(4-5):351-60 (2008).
Schwalfenberg, "Omega-3 fatty acids: their beneficial role in cardiovascular health," *Can Fam Physician*, 52: 734-740 (2006).
Takaki et al., "Anti-inflammatory and antinociceptive effects of *Rosmarinus officinalis* L. essential oil in experimental animal models," *Journal of Medicinal Food*, 11(4): 741-746 (2008).
Watts et al., "Regulation of endothelial nitric oxide synthase by PPAR agonists: molecular and clinical perspectives," Arterioscler Thromb Vasc Biol. 24(4):619-21 (2004).

\* cited by examiner

COMPOSITIONS CONTAINING OMEGA-3 OIL AND USES THEREOF

CROSS REFERENCE TO RELATED APPLICATIONS

This application is a Continuation of U.S. application Ser. No. 14/706,506, filed May 7, 2015, which is a Continuation of U.S. application Ser. No. 13/822,517, filed Apr. 12, 2013, which is the U.S. National Stage of International Application No. PCT/US2011/51698, filed Sep. 15, 2011, which claims benefit of U.S. Provisional Application No. 61/383,972, filed Sep. 17, 2010, each of which is hereby incorporated by reference.

FIELD OF THE INVENTION

The present invention relates to the field of pharmacology and molecular medicine. More specifically, the invention relates to pharmaceutical compositions containing omega-3 oil in co-solvents that are useful for treating, e.g., cardiovascular conditions, and/or as vehicles for delivering other therapeutic agents.

BACKGROUND OF THE INVENTION

Omega-3 oil is widely regarded as having certain therapeutic benefits primarily associated with cardiovascular disease. As the scientific community has become more comfortable with the safety and efficacy of omega-3 oils, the recommended daily dose has risen from less than a gram per day to over 8 grams per day. Omega-3 oils are essentially non-toxic and doses exceeding 20 grams per day have been taken over prolonged dosing periods without side effects. As high doses and high concentrations of omega-3 oils are required for therapeutic benefit, processes to enhance the absorption of omega-3 oil, to decrease the absorption time, and to increase the maximum peak concentration achieved in human blood are desired.

Desirable omega-3 oil compositions must contain high concentrations of the established active therapeutic fatty acids: eicosapentaenoic acid (EPA) and docosahexanoic acid (DHA). Omega-3 oil compositions should also be rapidly absorbed so that EPA and DHA can compete effectively with other fatty acids (e.g., omega-6 fatty acids) for integration and storage in cell membranes and in tissue triglyceride storage forms, which later are broken down to provide free EPA and DHA. Current practice suggests the use of liquid formulations containing, minimally 3.5 grams of active oil (combined EPA and DHA) in a reasonable volume for ingestion (e.g., 10 mL). For patients to comply with a once-a-day regime, the oil must have an acceptable taste and induce little or no nausea, intestinal discomfort, or regurgitation.

Based on current literature, the optimal dose of EPA and DHA is approximately 4 grams per day given at a single dosing. It is difficult to ingest enough gel capsules to achieve this dosage. Compliance and swallowing difficulties limit the ability of many patients from consistently taking an amount of omega-3 oil sufficient to elicit a therapeutic effect. High grade liquid oils are available that allow patients to take these quantities of oils, but the dose volume, taste, and costs are negative factors. Costs become prohibitive when chemically-altered or refined omega-3 oils from the natural state are used. The weakness in the available oil products is that these compositions have not been optimized for absorption.

High grade omega-3 oils, such as Maine Natural Health's OmegaMaine product lines, Nordic Naturals liquid formulations, and Carlsson liquid omega-3 product, are presently available. Of these products, Maine Natural Health's product is the only product that can deliver 3.5 grams of active combined EPA and DHA in a volume as little as 10 mL. Reducing the volume of the unit dose required for therapeutic benefit will increase patient compliance (especially in patients having dysphagia). The optimal unit dosage may be dispensed in an easy to administer volume, e.g., 2 teaspoons or 10 mL. Despite the high quality of omega-3 oil contained within these products, the absorption efficiencies (time to maximum plasma concentration, $t^{1/2}$ for absorption) of the products are not optimal. It is desirable to achieve high initial plasma concentrations to optimize the incorporation of the active omega-3 oils into cell membrane lipid bilayers and triglyceride stores.

The other marketed omega-3 products are also not optimized for absorption. Omacor or Lovaza is the only FDA-approved ethyl ester derivative of EPA. It is prescribed for patients with very high triglycerides and is administered in four large gel caps on a daily basis. When taken by oral ingestion, these large gel caps are dissolved (dissolution rate dependent step), de-esterified to fatty acids, and then absorbed. The conditions for dissolution and absorption are not optimal for these products, and thus, the efficiency of integration into cell membranes and triglyceride storage forms is not optimal.

Dietary supplements containing omega-3 oils, formulated as both gel caps and liquid formulations, are also available. The gel caps are inferior to Lovaza/Omacor (described above) and also suffer from a reduced efficiency of absorption. Thus, compositions containing omega-3 oils with improved efficiency of absorption are needed.

SUMMARY OF THE INVENTION

In a first aspect, the invention provides compositions containing omega-3 oil in a non-hydrophilic co-solvent containing an herbal-based oil, vitamin E, medium chain triglycerides (MCTs), lecithin, and phosphatidylcholine. Any of the compositions described herein may be formulated as a liquid (e.g., formulated for oral administration). In the provided compositions, the omega-3 oil may be from a natural source (e.g., salmon, herring, mackerel, and sardines), may be high grade (e.g., OmegaMaine omega-3 oils), may be an alkyl ester of a fatty acid (e.g., an alkyl ester of EPA and/or an alkyl ester of DHA), may be in the form of triglycerides, and/or may be a mixture of triglycerides and free fatty acids. In certain embodiments, the provided compositions are formulated in a dose containing greater than 3.0 g combined EPA and DHA in 10 mL (e.g., in a liquid formulation). In different embodiments of the above compositions, the non-hydrophilic co-solvent is less than 30% of the composition's total mass, the herbal-based oil (e.g., rosemary oil, basil oil, turmeric oil, and ginger oil) is 1% to 10% of the composition's total mass (e.g., between 3% to 5% of the composition's total mass), and/or amount of vitamin E present in a single dose is between 13.4 to 134 mg or is 1.3% to 13.4% of the composition's total mass.

In any of the above compositions, the MCTs (e.g., MCTs from coconut oil) are between 1% to 10% (e.g., 5%) of the composition's total mass and/or the phosphatidylcholine is 2% to 6% of the composition's total mass. Additional embodiments of the above compositions may further contain one or more nitric oxide-stimulating or -releasing agent(s) (e.g., arginine, a di-arginine, and citrulline), glucosamine, ethanol, and/or a Tween surfactant (e.g., Tween-80, Tween-60, Tween-40, and Tween-20). For example, any of the above compositions may contain rosemary oil and glucosamine, or may contain ethanol and Tween surfactant.

Additional embodiments of the above compositions may further contain one or more therapeutic organic molecule(s) (e.g., a NSAID, such as ketoprofen, ibuprofen, diflusinal, diclofenac, and naproxen), a DMARD (e.g., methotrexate), fenofibrate, a statin, niacin, and/or a H-1 antihistamine) with a molecular weight between 100 g/mole and 800 g/mole, a log P value greater than 2, or a melting point below 200° C. Such compositions containing one or more therapeutic organic molecule(s) may further contain ethanol and a Tween surfactant. For example, a dose of any of the above compositions may contain 5 mg/mL to 20 mg/mL (10 mg/mL to 15 mg/mL) fenofibrate and/or 1 mg/mL to 4 mg/mL of a statin (e.g., 0.5 mg/mL to 2 mg/mL of a statin). In various embodiments, the above compositions may further contain a DMARD, a NSAID, rosemary oil, and/or glucosamine. In additional examples of the above compositions, the H-1 antihistamine is from the tricyclic class of antihistamines (e.g., imipramine and doxepin) or from the non-tricyclic class of antihistamines (e.g., diphenhydramine and triprolidine).

Any of the above compositions may further contain one or more agents selected from: phosphatidylcholine, phosphatidylethanolamine, phosphatidylinositol, and phosphatidic acid. For example, a composition of the invention may contain phosphatidylinositol and phosphatidic acid. In additional embodiments of the compositions, 10% of the omega-3 oil is in solution and the remaining 90% of the omega-3 oil is in stable suspension form.

In one embodiment, the composition contains: 70% to 80% w/w of natural fish oil as a source of omega-3 oil; 5% to 15% w/w coconut oil as a source of MCTs; 0.5% to 5% w/w polytocopherol as a source of vitamin E; 1% to 10% w/w absolute ethanol; 1% to 10% w/w sorbital laurate; and 1% to 10% w/w cremaphor. In another embodiment, the composition contains: 70% to 80% w/w natural fish oil as a source of omega-3 oil; 5% to 15% w/w coconut oil as a source of MCTs; 0.5% to 5% w/w polytocopherol as a source of vitamin E; 1% to 5% w/w absolute ethanol; and 5% to 15% cremaphor.

In a further embodiment, the composition contains: 65% to 75% w/w of natural fish oil as a source of omega-3 oil; 1% to 10% w/w of coconut oil as a source of MCTs; 0.5% to 5% w/w polytocopherol as a source of vitamin E; 1% to 10% w/w absolute ethanol; 1% to 10% w/w sorbital laurate; 1% to 10% w/w cremaphor; and 1% to 10% w/w of a therapeutic organic molecule. In another embodiment, the composition contains: 65% to 75% w/w of natural fish oil as a source of omega-3 oil; 1% to 10% of coconut oil as a source of MCTs; 0.5% to 5% w/w polytocopherol as a source of vitamin E; 1% to 5% w/w absolute ethanol; 1% to 10% w/w sorbital laurate; 1% to 15% cremaphor; and 1% to 10% w/w of a therapeutic organic molecule.

The invention further provides kits containing one or more of the above compositions and instructions for administering these composition(s) to a subject. In various embodiments, the kits may further contain at least one additional composition containing a NSAID, a DMARD, or an H-1 antihistamine. In various embodiments of these kits, the additional H-1 antihistamine is from the tricyclic class of antihistamines (e.g., imipramine or doxepin) or is from the non-tricyclic class of antihistamines (e.g., diphenhydramine or tripolidine).

The invention further provides methods of decreasing the likelihood of developing a cardiovascular disease by administering to a subject any of the above compositions for a time and in an amount to reduce triglyceride or low-density lipoprotein (LDL) cholesterol levels in the blood of the subject, or to increase the amount of omega-3 oil present in the cell membranes of red blood cells in the subject. In various embodiments of these methods, the composition (e.g., formulated as a liquid) is administered once a day (e.g., orally administered, such as in the form of a liquid). In various embodiments of the methods, the composition is administered in a dose containing greater than 3.0 g combined EPA and DHA in 10 mL.

Desirably, the administering of one or more of the above composition(s) results in at least a 10% decrease in triglyceride or LDL cholesterol levels in the blood of the subject, at least a 10% increase in the amount of omega-3 oil present in the cell membranes of red blood cells in the subject, at least a 5% decrease in blood pressure in the subject, and/or a reduction in nausea or esophageal reflux compared to the nausea or esophageal reflux observed following administration of omega-3 oils alone.

The invention further provides methods for decreasing the triglyceride or low-density lipoprotein (LDL) cholesterol levels in a subject by administering one or more of the above composition(s) to the subject. In various embodiments of these methods, the composition (e.g., formulated as a liquid) is administered once a day (e.g., orally administered, such as in the form of a liquid). In various embodiments of the methods, the composition is administered in a dose containing greater than 3.0 g combined EPA and DHA in 10 mL.

Desirably, the administering of one or more of the above composition(s) results in at least a 10% decrease in triglyceride or LDL cholesterol levels in the blood of the subject, at least a 10% increase in omega-3 oil present in the cell membranes of red blood cells in the subject, and/or results in a reduction in nausea or esophageal reflux compared to the nausea and esophageal reflux observed following administration of omega-3 oils alone.

In another aspect, the invention provides methods of treating diabetes comprising administering one or more of the above composition(s) for a time and in an amount sufficient to increase insulin sensitivity in the subject or increase high density lipoprotein (HDL) cholesterol levels in the blood of the subject. In various embodiments of these methods, the composition administered contains phosphatidylinositol, phosphatidic acid, phosphatidylethanolamine, and/or phosphatidylserine (e.g., phosphatidylinositol and phosphatidic acid). In additional embodiments of these methods, the composition (e.g., formulated as a liquid) is administered once a day (e.g., orally administered, such as in the form of a liquid). In further embodiments of these methods, the composition is administered in a dose containing greater than 3.0 g combined EPA and DHA in 10 mL.

Desirably, the administering of one or more of the above composition(s) results in at least a 10% increase in insulin sensitivity in the subject or at least a 10% increase in HDL cholesterol levels in the blood of the subject.

The invention also provides methods of decreasing pain or inflammation in a subject by administering one or more of the above composition(s) to a subject. In various embodiments of these methods, the composition contains an NSAID and/or a DMARD, or rosemary oil and glucosamine. In various embodiments of these methods, the composition (e.g., formulated as a liquid) is administered once a day (e.g., orally administered, such as in the form of a liquid). In various embodiments of the methods, the composition is administered in a dose containing greater than 3.0 g combined EPA and DHA in 10 mL. In different embodiments of these methods, the one or more above composition(s) is administered at the same time as a NSAID or a DMARD, or is administered prior to a NSAID or a DMARD.

Desirably, the administering of one or more of the above composition(s) results in at least a 5% reduction in pain score, at least a 5% reduction in cyclooxygenase (COX)-1 or COX-2 activity, at least a 5% reduction in white blood cell count, or at least a 5% reduction in C-reactive protein, interleukin-6, and/or TNF-α levels, at least a 2-fold decrease in the time to optimal therapeutic effect, and/or the formation of less gastric lesions than administration of a NSAID or a DMARD alone.

In another aspect, the invention provides methods of treating a chronic pulmonary disease (e.g., asthma and chronic obstructive pulmonary disease) or irritable bowel syndrome, or reducing one or more symptoms of an autoimmune disease (e.g., multiple sclerosis and lupus erythematosus) by administering to the subject one or more of the above composition(s). In additional embodiments of these methods, the composition further contains a NSAID, a DMARD, rosemary oil, and/or glucosamine. In various embodiments of these methods, the composition contains an NSAID and/or a DMARD, or rosemary oil and glucosamine. In additional embodiments of these methods, the composition (e.g., formulated as a liquid) is administered once a day (e.g., orally administered, such as in the form of a liquid). In further embodiments of these methods, the composition is administered in a dose containing greater than 3.0 g combined EPA and DHA in 10 mL. In examples of these methods, the one or more composition(s) is administered at the same time as an NSAID or a DMARD, or is administered prior to a NSAID or a DMARD.

Desirably, these methods result in at least a 2-fold decrease in the time to optimal therapeutic effect or result in less gastric lesions than administration of a NSAID or a DMARD alone.

The invention further provides methods of formulating an omega-3 oil-containing pharmaceutical compositions having at least a 10% increase in absorption rate relative to the absorption rate of omega-3 oil alone, requiring the step of combining an omega-3 oil with a co-solvent containing one or more solvents or agents selected from the group of: a herbal-based oil, vitamin E, MCTs, lecithin, phosphatidylcholine, glucosamine, ethanol, a Tween surfactant, phosphatidylserine, phosphatidylethanolamine, phosphatidylinositol, phosphatidic acid, natural fish oil, coconut oil, polytocopherol, sorbital laurate, and cremaphor. In certain embodiments of these methods, the co-solvent contains a herbal-based oil, vitamin E, MCTs, lecithin, and phosphatidylcholine. In additional embodiments of these methods, the co-solvent contains natural fish oil, coconut oil, polytocopherol, sorbital laurate, cremaphor, an amide of an intermediate (C-6 to C-12) chain fatty acid, an amide of a long chain (C-12 to C-24 fatty acid), lauric alcohol, and lauric acid.

The invention also provides methods of formulating a pharmaceutical composition containing omega-3 oil and one or more therapeutic organic molecule(s) having at least a 10% increase in absorption rate relative to the absorption rate of omega-3 oil alone or the one or more therapeutic organic molecule(s) alone, requiring the step of combining an omega-3 oil and one or more therapeutic organic molecule(s) with a co-solvent containing one or more solvents or agents selected from the group of: a herbal-based oil, vitamin E, MCTs, lecithin, phosphatidylcholine, glucosamine, ethanol, a Tween surfactant, phosphatidylserine, phosphatidylethanolamine, phosphatidylinositol, phosphatidic acid, natural fish oil, coconut oil, polytocopherol, sorbital laurate, cremaphor, an amide of an intermediate (C-6 to C-12) chain fatty acid, an amide of a long chain (C-12 to C-24 fatty acid), lauric alcohol, and lauric acid. In various examples of these methods, the co-solvent contains a herbal-based oil, vitamin E, MCTs, lecithin, and phosphatidylcholine. In additional examples of these methods, the co-solvent contains natural fish oil, coconut oil, polytocopherol, absolute ethanol, sorbital laurate, and cremaphor. In additional examples of these methods, the one or more therapeutic organic molecule(s) are first combined with the co-solvent to solubilize the one or more therapeutic organic molecule(s), and then omega-3 oil is added to form the pharmaceutical composition.

In further examples of these methods, the composition contains ethanol (e.g., contains ethanol, a Tween surfactant (e.g., Tween-80), MCTs, vitamin E, and lecithin).

By the term "omega-3 oil" is meant an oil that contains at least one (e.g., one, two, or three) fatty acid(s) containing a carbon-carbon double bond in the n-3 position (i.e., the third bond from the methyl end of the fatty acid). Non-limiting examples of fatty acids that may be present in an omega-3 oil include: all-cis-7,10,13-hexadecatrienoic acid; α-linolenic acid (ALA) (all-cis-9,12,15-octadecatrienoic acid); stearidonic acid (SDA) (all-cis-6,9,12,15-octadecatetraenoic acid); eicosatrienoic acid (ETE) (all-cis-11,14,17-eicosatrienoic acid); eicosatetraenoic acid (ETA) (all-cis-8,11,14,17-eicosatetraenoic acid); eicosapentaenoic acid (EPA) (all-cis-5,8,11,14,17-eicosapentaenoic acid); docosapentaenoic acid (DPA) (all-cis-7,10,13,16,19-docosapentaenoic acid); docosahexaenoic acid (DHA) (all-cis-4,7,10,13,16,19-docosahexaenoic acid); tetracosapentaenoic acid (all-cis-9,12,15,18,21-tetracosapentaenoic acid); and tetracosahexaenoic acid (nisinic acid) (all-cis-6,9,12,15,18,21-tetracosahexaenoic acid).

Natural sources of omega-3 oils include, but are not limited to, cold water oily fish e.g., salmon, tuna, herring, mackerel, anchovies, and sardines), pollock, cod, catfish, flounder, grouper, halibut, mahi mahi, orange roughy, red snapper, shark, swordfish, tilefish, plankton, algae, krill, green-lipped mussel, chia seeds, kiwifruit seeds, perilla seeds, flax seeds, lingonberry seeds, camelina seeds, purslane seeds, black raspberry seeds, hemp seeds, butternut, walnuts, pecan nuts, and hazel nuts.

By the term "herbal-based oil" is meant an oil extracted from a herb plant (e.g., rosemary, basil, turmeric, and ginger). The herbal-based oil may inhibit cyclooxgenase COX-1 or COX-2 activity (e.g., mediate at least a 5%, 10%, 15%, 20%, 25%, 30%, 35%, 40%, 45%, 50%, 60%, 70%, 80%, 90%, or 95% decrease in COX-1 and/or COX-2 activity). These herbal oils contain mixtures of low potency cyclooxygenase (COX-1 and/or COX-2) inhibitors. These multi-component mixtures are additive in their effects. They are also synergistic because the various molecular inhibitors act/bind to different molecular sites on the enzyme (i.e., COX-1 and/or COX-2) surface and change the intrinsic ability of these enzymes to function. Multiple site inhibitors make these oils effective as therapeutic agents. Final concentrations of herbal extract in pharmaceutical compositions between 1% and 10% (by weight) are optimal. Combinations of multiple (e.g., two, three, four, or five) herbals oils are useful and provide greater efficacy.

By the term "high grade omega-3 oil" is meant an omega-3 oil preparation that is substantially free of impurities (e.g., at least 70%, 75%, 80%, 85%, 90%, 95%, 96%, 97%, 98%, or 99% pure). For example, a high grade omega-3 oil may be purified to remove vitamin A, vitamin D, mercury, lead, polychlorinated biphenyls, and dioxins.

By the term "nitric oxide-stimulating or -releasing agent" is meant a molecule that stimulates nitric oxide production from a nitric oxide synthetase (NOS) (e.g., endothelial NOS, inducible NOS, and neuronal NOS) or a molecule that releases nitric oxide (e.g., natural degradation or enzyme-mediated degradation). A non-limiting example of a molecule that stimulates nitric oxide production is citrulline. Non-limiting examples of molecules that break down to release nitric oxide include arginine, di-arginine, nitroglycerin, organic nitrates (e.g., glyceryl trinitrate, isosobride dinitrate, and isosorbide-5-mononitrate), sodium nitroprusside, S-nitrosothiols (e.g., S-nitroso-N—N-acetylpenicillamine and S-nitrosoglutathione), sydnonimines (e.g., molsidomine and 3-morpholino-sydnonimine), NONOates (e.g., spermine NONOate), and furoxans.

By the term "Tween surfactant" is meant a nonionic detergent derived in part from polyethoxylated sorbitan. Non-limiting examples of Tween surfactants include Tween-20, Tween-40, Tween-60, and Tween-80.

By the term "non-steroidal anti-inflammatory drug" or "NSAID" is meant a non-steroidal agent that prevents or diminishes inflammation. NSAIDs include naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, tolmetin, and COX-2 inhibitors such as rofecoxib, celecoxib, valdecoxib, or lumiracoxib.

By the term "disease-modifying anti-rheumatic drug" or "DMARD" is meant a therapeutic agent used for the treatment of an inflammatory disease. Examples of DMARDs known in the art include, e.g., auranofin, aurothioglucose, azathioprine, chlorambucil, cyclophosphamide, D-penicillamine, gold sodium thiomalate (injectable gold), hydroxychloroquine, leflunomide, methotrexate, minocycline, mycophenolate mofetil, and sulfasalazine.

By the term "therapeutic organic molecule" is meant a molecule that may be used to reduce the likelihood (e.g., at least a 5%, 10%, 15%, 20%, 25%, 30%, 35%, 40%, 45%, 50%, 60%, 70%, 80%, 90%, or 95% reduction) of developing a disease or to treat or ameliorate one or more symptoms of a disease in a subject (e.g., reduce the severity of one, two, three, four, or five symptoms by at least 5%, 10%, 15%, 20%, 25%, 30%, 35%, 40%, 45%, 50%, 60%, 70%, 80%, 90%, or 95%). A therapeutic organic molecule may have a molecular weight between 100 g/mole and 800 g/mole, a log P value greater than 2, or a melting point of below 200° C. In addition, therapeutic organic molecules may be soluble in a hydrophobic environment (e.g., a solvent). Non-limiting examples of therapeutic organic molecules include NSAIDs (e.g., ketoprofen), DMARDs (e.g., methotrexate), fenofibrate, a statin, and niacin.

By the phrase "decreasing the likelihood of developing" is meant a reduction (e.g., at least 5%, 10%, 15%, 20%, 25%, 30%, 35%, 40%, 50%, 60%, 70%, 80%, 90%, or 95%) for a subject or a patient population in the chance or rate of developing a specific disease (e.g., cardiovascular disease) by administering one or more pharmaceutical compositions compared to a subject or patient population not receiving the one or more pharmaceutical compositions. The methods of the invention may also reduce the likelihood of developing one or more (e.g., one, two, three, four, or five) symptoms of a disease (e.g., cardiovascular disease or diabetes) in a patient population or a subject receiving one or more of the provided pharmaceutical compositions.

By "treating" a disease in a subject is meant reducing the severity or duration of at least one symptom (e.g., one, two, three, four, or five symptoms) of the disease by administrating one or more pharmaceutical composition(s) to the subject.

By the phrase "one or more symptoms of cardiovascular disease" is meant one or more symptoms clinically observed for patients having cardiovascular disease. Non-limiting examples of symptoms of cardiovascular disease include: shortness of breath, heart palpitations, increased heart rate, increased blood pressure, weakness, dizziness, nausea, sweating, atherosclerotic plaques in artery walls, elevated low-density lipoprotein (LDL) cholesterol levels (e.g., greater than 70 mg/dL, 100 mg/dL, 130 mg/dL, 150 mg/dL, or 200 mg/dL), decreased high-density lipoprotein (HDL) cholesterol levels (e.g., less than 50 mg/dL or less than 40 mg/dL), and increased triglyceride levels (e.g., greater than 150 mg/dL).

By the phrase "one or more symptoms of diabetes" is meant one or more symptoms clinically observed for patients having diabetes (e.g., type I diabetes, type II diabetes, or pre-diabetes). Non-limiting examples of symptoms of diabetes include: frequent urination, unusual thirst, extreme hunger, unusual weight loss, extreme fatigue and irritability, frequent infections, blurred vision, tingling/numbness in extremities, recurring infections (e.g., skin, gum, and bladder infections), decreased insulin absorption or sensitivity (e.g., decrease by at least 10%, 15%, 20%, 25%, 30%, 35%, 40%, 45%, 50%, 55%, or 60%), elevated blood glucose levels (e.g., one or more blood glucose readings of greater than 104 mg/dL), and increased glycated hemoglobin levels (e.g., $HbA_{1C}$ greater than 7.0%).

By the phrase "decreasing the triglyceride or low-density lipoprotein cholesterol levels" is meant a reduction of at least 5% (e.g., at least 10%, 15%, 20%, 25%, 30%, 35%, 40%, 45%, 50%, 55%, 60%, 65%, or 70%) in the triglyceride levels or LDL cholesterol levels in a subject compared to the triglyceride or LDL cholesterol levels in the subject prior to treatment or a subject or patient population not receiving therapeutic treatment. For a human, the normal triglyceride level is <150 mg/dL and the normal LDL cholesterol level is 25 mg/dL to <70 mg/dL. A decrease in triglyceride level may result in a reduction of an elevated triglyceride level (e.g., greater than or equal to 150 mg/dL) to a triglyceride level within the normal range (e.g., less than 150 mg/dL). A decrease in LDL cholesterol level may result in a reduction of an elevated LDL cholesterol level (e.g., greater than or equal to 70 mg/dL or greater than or equal to 100 mg/dL) to a LDL cholesterol level within the normal range (e.g., 25 mg/dL to <70 mg/dL).

By the term "diabetes" is meant both type I diabetes (juvenile-onset or diabetes mellitus) and type II diabetes (adult-onset diabetes). The term diabetes is also meant to include those individuals designated as being "pre-diabetic" or indicated as having a propensity to develop type II diabetes based on the presentation of one or more (e.g., one, two, three, or four) of the following symptoms: increased weight (obesity), decreased insulin absorption or sensitivity (e.g., decrease by at least 5%, 10%, 15%, 20%, 25%, 30%, 35%, 40%, 45%, 50%, 55%, or 60%), elevated blood glucose levels (e.g., one or more blood glucose readings greater than 104 mg/dL), and increased glycated hemoglobin levels (e.g., $HbA_{1C}$ greater than 7.0%). Treatment of diabetes may result in an increase (e.g., by at least 5%, 10%, 15%, 20%, 25%, 30%, 35%, 40%, 45%, 50%, 55%, 60%, 70%, 80%, 90%, or 95%) in insulin absorption or sensitivity, a decrease (e.g., by at least 5%, 10%, 15%, 20%, 25%, 30%, 35%, 40%, 45%, 50%, 55%, or 60%) in blood glucose levels in a subject or patient population having elevated blood glucose (e.g., one or more blood glucose readings greater than 104 mg/dL), and a decrease (e.g., by at least 5%, 10%, 15%, 20%, 25%, or 30%) in glycated hemoglobin levels in a subject or patient population having increased glycated hemoglobin levels (e.g., $HbA_{1C}$ greater than 7.0%).

By the term "decreasing pain in a subject" is meant a decrease (e.g., at least 5%, 10%, 15%, 20%, 25%, 30%, 35%, 40%, 45%, 50%, 55%, 60%, 65%, 70%, 80%, 90%, or 95%) in the pain score of a subject or patient population receiving therapeutic treatment compared to the pain score of a subject or patient population prior to treatment or the pain score of a subject or patient population not receiving the therapeutic treatment. Non-limiting examples of tests to quantify pain in a subject include: Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnare, Wong-Baker FACES Pain Rating Scale, and Visual Analog Scale (VAS). A decrease in pain may result in at least a 5% decrease (e.g., at least a 10%, 15%, 20%, 25%, 30%, 35%, 40%, 45%, 50%, 55%, 60%, 70%, 80%, 90%, or 95% decrease) in one or more (e.g., one, two, three, or four) of the pain scores listed above.

By the term "decreasing inflammation in a subject" is meant a decrease (e.g., at least 5%, 10%, 15%, 20%, 30%, 35%, 40%, 45%, 50%, 55%, 60%, 65%, 70%, 80%, 90%, or 95% decrease) in the severity or duration of one or more symptoms (e.g., one, two, three, four, or five symptoms) of inflammation in a subject receiving treatment compared to the severity or duration of one or more symptoms of inflammation in the subject prior to treatment or the severity or duration of one or more symptoms of inflammation in a subject or patient population not receiving therapeutic treatment. Non-limiting examples of symptoms of inflammation include: increased (e.g., by at least 5%, 10%, 15%, 20%, 25%, 30%, 35%, 40%, 45%, 50%, 55%, 60%, 70%, 80%, 90%, or 95%) COX-1 and/or COX-2 activity, increased (e.g., by at least 5%, 10%, 15%, 20%, 25%, 30%, 35%, 40%, 45%, 50%, 55%, 60%, 70%, 80%, 90%, or 95%) white blood cell count, increased (e.g., by at least 5%, 10%, 15%, 20%, 25%, 30%, 35%, 40%, 45%, 50%, 55%, 60%, 70%, 80%, 90%, or 95%) C-reactive protein, interleukin-6, and/or TNF-alpha levels, swelling, pain, and increased (e.g., by at least 5%, 10%, 15%, 20%, 25%, 30%, 35%, 40%, 45%, 50%, 55%, 60%, 70%, 80%, 90%, or 95%) erythrocyte sedimentation rate. The methods of the invention may result in a reduction (e.g., by at least 5%, 10%, 15%, 20%, 25%, 30%, 35%, 40%, 45%, 50%, 55%, 60%, 70%, 80%, 90%, or 95%) in COX-1 and/or COX-2 activity, a decrease (e.g., by at least 5%, 10%, 15%, 20%, 25%, 30%, 35%, 40%, 45%, 50%, 55%, 60%, 70%, 80%, 90%, or 95%) in the white blood cell count, a decrease (e.g., by at least 5%, 10%, 15%, 20%, 25%, 30%, 35%, 40%, 45%, 50%, 55%, 60%, 70%, 80%, 90%, or 95%) in C-reactive protein levels, decreased swelling, decreased pain (e.g, at least a 5%, 10%, 15%, 20%, 25%, 30%, 35%, 40%, 45%, 50%, 60%, 70%, 80%, 90%, or 95% decrease in one or more (e.g., one, two, three, four, or five) of the pain scores listed above), and a decrease (e.g., by at least 5%, 10%, 15%, 20%, 25%, 30%, 35%, 40%, 45%, 50%, 55%, 60%, 70%, 80%, 90%, or 95%) in erythrocyte sedimentation rate.

By "symptoms of autoimmune disease" is meant one or more symptoms clinically observed for patients having an autoimmune disease (e.g., multiple sclerosis and lupus erythematosus). Non-limiting examples of symptoms of autoimmune disease include pain (e.g., joint pain), inflammation, and loss of motor function.

The recitation herein of numerical ranges by endpoints is intended to include all numbers subsumed within that range (e.g., a recitation of 1 to 5 includes 1, 1.5, 2, 2.75, 3, 3.80, 4, and 5).

As used herein, "a" or "an" means "at least one" or "one or more" unless otherwise indicated. In addition, the singular forms "a", "an" and "the" include plural referents unless the context clearly dictates otherwise. Thus, for example, reference to a composition containing "a compound" includes a mixture of two or more compounds.

Other features and advantages of the invention will be apparent from the following description of the preferred embodiments thereof, and from the claims.

DETAILED DESCRIPTION

We have discovered a new method for formulating compositions containing omega-3 oils that allow for an increased rate of absorption in mammals (e.g., humans). The invention therefore provides compositions containing omega-3 oils that exhibit increased absorption rates, kits containing these compositions, and methods for decreasing the likelihood of developing cardiovascular disease, decreasing triglyceride or LDL cholesterol levels, decreasing blood pressure, decreasing pain or inflammation, treating diabetes, chronic pulmonary diseases (e.g., asthma and chronic obstructive pulmonary disease), and irritable bowel syndrome, and decreasing one or more symptoms of an autoimmune disease (e.g., multiple sclerosis and lupus erythematosus.

Pharmaceutical Compositions

The invention provides pharmaceutical compositions containing omega-3 oils in a non-hydrophilic co-solvent system or kit that have increased absorption rates. The omega-3 oils included in the pharmaceutical compositions may be obtained from a natural source, including, for example, cold water oily fish (e.g., salmon, tuna, herring, mackerel, anchovies, and sardines), pollock, cod, catfish, flounder, grouper, halibut, mahi mahi, orange roughy, red snapper, shark, swordfish, tilefish, plankton, algae, krill, green-lipped mussel, chia seeds, kiwifruit seeds, perilla seeds, flax seeds, lingonberry seeds, camelina seeds, purslane seeds, black raspberry seeds, hemp seeds, butternut, walnuts, pecan nuts, and hazel nuts. The omega-3 oil included in the pharmaceutical compositions may be high grade (e.g., at least 70%, 75%, 80%, 85%, 90%, 91%, 92%, 93%, 94%, 95%, 96%, 97%, 98%, or 99% pure). In one example, the high grade omega-3 oil used in the pharmaceutical compositions is OmegaMaine omega-3 oils. In additional non-limiting examples of the pharmaceutical compositions, the omega-3 oil is at least 25% (e.g., at least 30%, 35%, 40%, 45%, 50%, 55%, 65%, 70%, 75%, 80%, 85%, 90%, or 95%) of the composition's total mass. In one implementation of the invention, at least 10% (e.g., at least 15%, 20%, 25%, 30%, 35%, 40%, 45%, or 50%) of the omega-3 oil in the composition is in solution and at least 50% of the omega-3 oil in the composition is in stable suspension form (e.g., at least 55%, 60%, 65%, 70%, 75%, 80%, 85%, 90%, or 95%). The omega-3 oil is typically a mixture of one or more omega-3 fatty acids, including EPA, DHA, or a combination thereof. The omega-3 oil may contain an alkyl ester of a fatty acid (e.g., an alkyl ester of eicosapentaenoic acid and docosahexanoic acid) or may be in the form of free fatty acids and/or triglycerides. In other embodiments, the omega-3 oil is a mixture of triglycerides and free fatty acids.

The co-solvent in the pharmaceutical compositions may include one or more (e.g., two, three, four, five, six, seven, eight, nine, or ten) solvents or agents that enhance the absorption rate of omega-3 oils in a mammal (e.g., a human), including, but not limited to: herbal-based oil (e.g., rosemary oil, basil oil, turmeric oil, and ginger oil), vitamin E, medium chain triglycerides (MCTs), lecithin, phosphatidylcholine, glucosamine, ethanol, Tween surfactant (e.g., Tween-20, Tween-40, Tween-60, and Tween-80), phosphatidylserine, phosphatidylethanolamine, amides of intermediate (C-8 to C-12) fatty acids, amide of long chain fatty acids (C-13 to C-24), lauric alcohol, lauric acid, phosphatidylinositol, phosphatidic acid, natural fish oil, coconut oil, polytocopherol, sorbital laurate, and cremaphor. Suitable ingredients are defined in Example 1 given below and by Formulas 1 and 2 within Example 1. In non-limiting examples of the pharmaceutical compositions, the co-solvent is less than 30% (e.g., less than 25%, 20%, 15%, 10%, or 5%) of the composition's total mass. In one example, the compositions contains a herbal-based oil (1% to 10% or 3% to 5% of the composition's final mass). In another example, the composition contains vitamin E (1.3% to 13.4% of the composition's final mass or 13.4 mg to 134 mg per dose).

The pharmaceutical compositions may further include one or more (e.g., one, two, three, four, or five) nitric oxide-stimulating or -releasing agents. Non-limiting examples of such nitric oxide-stimulating or -releasing agents include: citrulline, arginine, di-arginine, nitroglycerin, organic nitrates (e.g., glyceryl trinitrate, isosobride dinitrate, and isosorbide-5-mononitrate), sodium nitroprusside, S-nitrosothiols (e.g., S-nitroso-N—N-acetylpenicillamine and S-nitrosoglutathione), sydnonimines (e.g., molsidomine and 3-morpholino-sydnonimine), NONOates (e.g., spermine NONOate), and furoxans.

The pharmaceutical compositions may further include one or more (e.g., one, two, three, four, or five) therapeutic organic molecule(s). For example, the therapeutic organic molecules may have a molecular weight between 100 g/mole and 800 g/mole (e.g., between 100 g/mole and 400 g/mole, between 400 g/mole and 800 g/mole, between 200 g/mole and 700 g/mole, and between 300 g/mole and 600 g/mole), a log P value greater than 2 (e.g., greater than 2.5, greater than 3.0, greater than 3.5, and greater than 4.0), and/or a melting point of below 200° C. (e.g., below 180° C., below 160° C., and below 140° C.). Non-limiting examples of therapeutic organic molecules that may be included in the pharmaceutical compositions include NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, tolmetin, and COX-2 inhibitors (e.g., rofecoxib, celecoxib, valdecoxib, and lumiracoxib)) and DMARDs (e.g., auranofin, aurothioglucose, azathioprine, chlorambucil, cyclophosphamide, D-penicillamine, gold sodium thiomalate (injectable gold), hydroxychloroquine, leflunomide, methotrexate, minocycline, mycophenolate mofetil, and sulfasalazine). Additional examples of therapeutic organic molecules are known in the art (e.g., fenofibrate, statins, niacin, additional NSAIDs, and additional DMARDs). More than one (e.g., two, three, four, or five) of the above compositions may be administered for additional therapeutic benefit. Further, the NSAID class therapeutic may be combined with one or more (e.g., two, three, four, or five) antihistamine(s) or one or more (e.g., two, three, four, or five) antihistamine(s) that have H-1 receptor antagonist properties. Non-limiting examples of H-1 antihistamines include non-tricyclic antihistamines (e.g., diphenhydramine and triprolidine) and tricyclic antihistamines (e.g., doxepin and imprarnine). Non-limiting examples of compositions containing one or more therapeutic organic molecule(s) contain a Tween surfactant (e.g., Tween-80, Tween-60, Tween-40, and Tween-20) and ethanol.

In one example of a pharmaceutical composition according to the invention, the non-hydrophilic co-solvent contains the combination of a herbal-based oil (e.g., rosemary oil, basil oil, turmeric oil, and ginger oil), vitamin E (e.g., in purified or unpurified form (e.g., polytocopherol)), medium chain triglycerides (e.g., in purified or unpurified form (e.g., coconut oil)), lecithin, and phosphatidylcholine (e.g., in purified or unpurified form (e.g., a natural lipid composition)). In this example, the herbal-based oil is at least 1% to 5% of the composition's total mass (e.g., 2% to 4%), the amount of vitamin E present in a single dose of the composition is between 13.4 mg to 134 mg (e.g., 40 mg to 120 mg, 50 mg to 100 mg, 15 mg to 60 mg, and 60 mg to 134 mg), the MCTs are between 1% to 10% of the composition's total mass (e.g., between 1% and 5%, between 5% and 10%, between 2% and 8%, between 3% and 7%, and between 4% and 6%), and the phosphatidylcholine is between 0.5% and 10% of the composition's total mass (e.g., between 2% and 8%, between 3% and 7%, between 4% and 6%, between 1% and 5%, and between 5% and 10%). Additional examples of pharmaceutical compositions are similar to this example, except that they further include in the co-solvent system a Tween surfactant (e.g., Tween-80, Tween-60, Tween-40, and Tween-20) and/or ethanol (e.g., absolute ethanol). Other examples of pharmaceutical compositions are identical to the above examples specified in this paragraph, except that they further include in the non-hydrophilic co-solvent rosemary oil and/or glucosamine. Further examples of pharmaceutical compositions are similar to the above examples in this paragraph, except that they further include one or more (e.g., one, two, three, or four) of phosphatidylserine, phosphatidylethanolamine, phosphatidylinositol, and phosphatidic acid (e.g., phosphatidylinositol and phosphatidic acid). In any of the above examples in this paragraph, the pharmaceutical compositions may further include one or more (e.g., one, two, three, four, or five) nitric oxide-stimulating or -releasing agents (see, examples above) and/or one or more (e.g., one, two, three, four, or five) therapeutic organic molecules, such NSAIDs (e.g., ketoprofen) or DMARDs (e.g., methotrexate).

Additional examples of the provided pharmaceutical compositions contain 70% to 80% w/w of natural fish oil as a source of omega-3 oil, 5% to 15% w/w of coconut oil as a source of MCTs, 0.5% to 5% w/w of polytocopherol as a source of vitamin E, 1% to 10% w/w of absolute ethanol, 1% to 10% w/w of sorbitol laurate, and/or 1% to 10% w/w cremaphor. Another example, of the composition contains 70% to 80% w/w natural fish oil as source of omega-3 oil, 5% to 15% w/w of coconut oil as a source of MCTs, 0.5% to 5% w/w of polytocopherol as a source of vitamin E, 1% to 5% w/w of absolute ethanol, 1% to 10% w/w of sorbitol laurate, and/or 5% to 15% w/w cremaphor.

Further examples of the provided pharmaceutical compositions contain 65% to 75% w/w of natural fish oil as a source of omega-3 oil, 1% to 10% w/w coconut oil as a source of MCTs, 0.5% to 5% w/w of polytocopherol as a source of vitamin E, 1% to 10% w/w of absolute ethanol, 1% to 10% w/w of sorbitol laurate, 1% to 10% w/w cremaphor, and/or 1% to 10% w/w of one or more (e.g., one, two, three, four, or five) therapeutic organic molecule(s) (e.g., ketoprofen, methotrexate, fenofibrate, statin, and/or niacin or combinations thereof). In another example, the composition contains 65% to 75% w/w of natural fish oil as a source of omega-3 oil, 1% to 10% w/w coconut oil as a source of MCTs, 0.5% to 5% w/w of polytocopherol as source of vitamin E, 1% to 5% w/w of absolute ethanol, 1% to 10% w/w of sorbital laurate, 1% to 15% w/w cremaphor, and/or 1% to 10% w/w of one or more (e.g., one, two, three, four, or five) therapeutic organic molecule(s) (e.g., ketoprofen, methotrexate, fenofibrate, statin, and/or niacin). For example, in a formulation of omega-3 oil and 1% ethanol, the fenobibrate dose/unit volume of the pharmaceutical composition will typically be in the range of 5 mg/mL to 20 mg/mL, more typically in the range of 10 mg/mL to 15 mg/mL. In the presence of absorption enhancers, this dose may be further lowered by at least 10% (e.g., by at least 15%, 20%, 25%, 30%, 35%, 40%, 45%, 50%, 55%, 60%, 65%, 70%, 75%, or 80%, or between 1 mg/mL to 10 mg/mL or 0.1 mg/mL to 5 mg/mL). Lowering the dose of FDA-approved therapeutics will lower the side effect profile while maintaining therapeutic efficacy. In the case of statins, the dose range/unit dose would be between 1 mg/mL and 4 mg/mL in the pharmaceutical composition. The typical dose would be between 0.5 mg/mL and 2 mg/mL in the pharmaceutical composition. In the presence of absorption enhancers this dose may be further lowered by at least 10% (e.g., at least 15%, 20%, 25%, 30%, 35%, 40%, 45%, 50%, 55%, 60%, 65%, 70%, 75%, or 80%). Liquid formulation of these drugs and all drugs in general will be less variable and more uniform because absorption efficiency will be improved, allowing the amount of drug product administered for a given therapeutic effect to be reduced. Sides effects related to dose strength should decrease because of the reduction in drug load.

A single dose of the provided pharmaceutical compositions may contain greater than 2.5 g (e.g., greater than 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g) combined of EPA and DHA. For example, a single dose of the pharmaceutical composition may contain greater than 2.5 g (e.g., greater than 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g) combined of EPA and DHA in a volume of at least 5.0 mL (e.g., at least 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL).

A single dose of the provided pharmaceutical composition may contain between 0.1 mg and 2.0 g (e.g., between 0.1 mg and 1.5 mg, 0.1 mg and 1 g, 0.1 mg and 750 mg, 1 mg and 650 mg, 1 mg and 550 mg, 1 mg and 500 mg, 10 mg and 450 mg, 10 mg and 400 mg, 10 mg and 350 mg, 10 mg and 350 mg, and 10 mg and 250 mg) of each of the one or more (e.g., one, two, three, four, or five) therapeutic organic molecules (e.g., a NSAID (e.g., ketoprofen), DMARD (e.g., methotrexate), fenofibrate, a statin, and niacin).

The compositions may be formulated using any known method, including oral formulations such as a pill (e.g., bilayered or trilayered pill), a fluid (e.g., suspension-based liquid or a multi-component clear liquid), a capsule, or a dietary supplement (e.g., a shake or bar). The compositions may also be formulated for intramuscular, intraocular, intranasal, subcutaneous, intraarterial, and intravenous administration. Desirable embodiments of the invention are formulated as a liquid oral composition. Such a liquid oral composition may be administered to a subject having dysphagia. An artisan may evaluate a matrix of possibilities to select the optimal formulation, which may be regarded as that solution that fully dissolves the drug product and provides the best PK/PD profile upon animal/human testing.

Kits

The invention further provides kits containing one or more (e.g., 1, 2, 3, 4, 5, 6, 7, 8, 9, or 10) of the pharmaceutical compositions described herein. Desirably, the pharmaceutical compositions included in the kits are formulated for oral administration. The kits may further contain materials to aid in the administration of the pharmaceutical compositions (e.g., a syringe). The kits may contain one or more doses of a pharmaceutical compositions provided by the invention. The kits may further contain instructions for administering the pharmaceutical compositions to a subject having a cardiovascular disease, a propensity to develop a cardiovascular disease, diabetes (e.g., type I or type II diabetes), inflammation, pain, elevated triglyceride levels, elevated blood pressure, chronic pulmonary disease (e.g., asthma and chronic obstructive pulmonary disease), irritable bowel syndrome, autoimmune disease (e.g., multiple sclerosis and lupus erythematosus), and/or elevated LDL cholesterol levels.

The kits may also include additional one or more (e.g., two, three, or four) additional compositions containing a DMARD, a NSAID, and/or an antihistamine (e.g., an H-1 receptor antihistamine). The instructions may indicate that the one or more additional compositions containing a DMARD and/or a NSAID are administered to the subject at the same time (co-administered) as the pharmaceutical compositions containing omega-3 oils (described above) or may indicate that the one or more additional compositions containing a DMARD and/or NSAID are delivered after administration (e.g., within 1 minute, 5 minutes, 10 minutes, 15 minutes, 20 minutes, 30 minutes, 45 minutes, 1 hour, 2 hours, 3 hours, 4 hours, 5 hours, 6 hours, 7 hours, 8 hours, 9 hours, 10 hours, or 12 hours) of the pharmaceutical compositions containing omega-3 oils described herein. The kits desirably contain compositions formulated as a liquid for oral administration.

Methods of Formulation

The invention further provides methods for formulating an omega-3 oil-containing pharmaceutical composition having an increased absorption rate relative to omega-3 oil alone, requiring the step of combining an omega-3 oil (e.g., purified or in a natural form (e.g., natural fish oil)) with a non-hydrophilic co-solvent. The non-hydrophilic co-solvent used to formulate the omega-3 containing pharmaceutical compositions may contain one or more (e.g., one, two, three, four, five, six, seven, eight, nine, or ten) solvents or agents that enhance the absorption rate of omega-3 oils in a mammal (e.g., a human), including, but not limited to: herbal-based oil (e.g., rosemary oil, basil oil, turmeric oil, and ginger oil), vitamin E, medium chain triglycerides (MCTs), lecithin, phosphatidylcholine, glucosamine, ethanol, Tween surfactant (e.g., Tween-20, Tween-40, Tween-60, and Tween-80), phosphatidylserine, phosphatidylethanolamine, amides of intermediate (C-8 to C-12) fatty acids, amides of long chain (C-12 to C-24) fatty acids, lauric alcohol, lauric acid, phosphatidylinositol, phosphatidic acid, natural fish oil, coconut oil, polytocopherol, sorbital laurate, and cremaphor. An amide of a medium chain or long chain fatty acid may be derived from a naturally-occurring amino acid (e.g., glycine, lysine, and alanine).

Also provided are methods for formulating a pharmaceutical composition containing omega-3 oil and one or more (e.g., one, two, three, four, or five) therapeutic organic molecules having an increased absorption rate relative to omega-3 oil alone or the one or more therapeutic organic molecules alone, requiring the step of combining an omega-3 oil (e.g., purified or in a natural form (e.g., natural fish oil)) and one or more therapeutic organic molecules with a non-non-hydrophilic co-solvent (described above). In additional examples of this method, the one or more therapeutic organic molecule(s) are first combined with the co-solvent (e.g., a co-solvent containing one or more of ethanol, a Tween surfactant (e.g., Tween-80, Tween-60, Tween-40, and Tween-20), MCTs, vitamin E, and/or lecithin) to solubilize the one or more therapeutic organic molecule(s), and then the omega-3 oil is added to form the pharmaceutical composition. In desirable embodiments of these methods, the resulting composition is a liquid that may be orally administered.

Methods of Treatment

The invention also provides methods for decreasing the likelihood of developing a cardiovascular disease, decreasing the triglyceride or LDL cholesterol levels, decreasing blood pressure, decreasing pain or inflammation, treating diabetes (e.g., type I diabetes, type II diabetes, or pre-diabetes), chronic pulmonary diseases (e.g., asthma and chronic obstructive pulmonary disease), or irritable bowel syndrome, reducing one or more symptoms of an autoimmune diseases (e.g., multiple sclerosis and lupus erythamatosus), or reducing one or more symptoms of allergic conditions (e.g., seasonal allergies or seasonal rhinitis where it is standard to administer an H-1 receptor antihistamine) in a subject comprising administering to the subject one or more (e.g., one, two, three, four, or five) of the pharmaceutical compositions described herein.

Methods for the diagnosis and/or monitoring of cardiovascular disease, triglyceride and LDL cholesterol levels, high blood pressure, pain, inflammation, chronic pulmonary diseases (e.g., asthma and chronic obstructive pulmonary disease), autoimmune diseases (e.g., multiple sclerosis and lupus erythematosus), and diabetes are known in the art. For example, a physician may monitor and/or diagnose cardiovascular disease based on the presentation of one or more of the following symptoms in a subject: shortness of breath, heart palpitations, increased heart rate, increased blood pressure, weakness, dizziness, nausea, sweating, atherosclerotic plaques in artery walls, elevated low-density lipoprotein (LDL) cholesterol levels (e.g., greater than 70 mg/dL or greater than 100 mg/dL), decreased high-density lipoprotein (HDL) cholesterol levels (e.g., less than 50 mg/dL or less than 40 mg/dL), and increased triglyceride levels (e.g., greater than 150 mg/dL or greater than 200 mg/dL). Triglyceride and LDL cholesterol levels in the blood of a subject may be monitored using known laboratory tests (e.g., a lipid profile test). Pain may be monitored by a physician using one or more pain score tests to quantify pain in a subject. Non-limiting examples of such pain score tests include: Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnaire, Wong-Baker FACES Pain Rating Scale, and Visual Analog Scale (VAS). A physician may monitor inflammation by measuring one or more of the following symptoms in a subject: increased (e.g., by at least 5%, 10%, 15%, 20%, 25%, 30%, 35%, 40%, 45%, 50%, 55%, 60%, 70%, 80%, 90%, or 95%) COX-1 and/or COX-2 activity, increased (e.g., by at least 5%, 10%, 15%, 20%, 25%, 30%, 35%, 40%, 45%, 50%, 55%, 60%, 70%, 80%, 90%, or 95%) white blood cell count, increased (e.g., by at least 5%, 10%, 15%, 20%, 25%, 30%, 35%, 40%, 45%, 50%, 55%, 60%, 70%, 80%, 90%, or 95%) C-reactive protein, interleukin-6, and/or TNF-α levels, swelling, pain, and increased (e.g., by at least 5%, 10%, 15%, 20%, 25%, 30%, 35%, 40%, 45%, 50%, 55%, 60%, 70%, 80%, 90%, or 95%) erythrocyte sedimentation rate. Diabetes may be monitored and/or diagnosed by a physician based on the presentation of the following symptoms: increased weight (obesity), decreased insulin absorption or sensitivity (e.g., decrease by at least 5%, 10%, 15%, 20%, 25%, 30%, 35%, 40%, 45%, 50%, 55%, or 60%), elevated blood glucose levels (e.g., one or more blood glucose readings greater than 104 mg/dL), and increased glycated hemoglobin levels (e.g., $HbA_{1C}$ greater than 7.0%).

The methods of the invention may be used to treat or decrease the likelihood of developing a cardiovascular disease. The provided methods may reduce the severity or duration (e.g., by at least 10%, 15%, 20%, 25%, 30%, 35%, 40%, 45%, 50%, 55%, 60%, 65%, 70%, 75%, 80%, 85%, 90%, 95%, or even 100%) of one or more (e.g., one, two, three, four, or five) of the symptoms of cardiovascular disease or prevent the onset of one or more (e.g., one, two, three, four, or five) of the symptoms of cardiovascular disease (e.g., compared to severity, duration, and number of symptoms observed in the subject prior to treatment or the severity, duration, and number of symptoms observed in a subject or patient population not receiving treatment). Non-limiting examples of symptoms of cardiovascular disease include: shortness of breath, heart palpitations, increased heart rate, increased blood pressure, weakness, dizziness, nausea, sweating, atherosclerotic plaques in artery walls, elevated low-density lipoprotein (LDL) cholesterol levels (e.g., greater than 70 mg/dL or greater than 100 mg/dL), decreased high-density lipoprotein (HDL) cholesterol levels (e.g., less than 50 mg/dL or less than 40 mg/dL), and increased triglyceride levels (e.g., greater than 150 mg/dL or greater than 200 mg/dL). In one example, the methods of the invention may result in one or more of the following effects: at least a 10% reduction (e.g., at least 15%, 20%, 25%, 30%, 35%, 40%, 45%, 50%, 55%, or 60%) in LDL cholesterol levels, at least a 10% increase (e.g., at least a 15%, 20%, 25%, 30%, 35%, 40%, 50%, 55%, or 60%) in HDL cholesterol levels, and/or at least a 10% decrease (e.g., at least 15%, 20%, 25%, 30%, 35%, 40%, 45%, 50%, 55%, or 60%) in triglyceride levels (relative to these levels in a subject prior to treatment or these levels in a subject or patient population not receiving treatment). The methods for treating or decreasing the likelihood of developing cardiovascular disease may also result in a decrease (e.g., by at least 5%, 10%, 15%, 20%, 25%, 30%, 35%, 40%, 45%, 50%, 55%, 60%, 65%, 70%, 75%, 80%, 85%, 90%, 95%, or 100%) in nausea and/or esophageal reflux (e.g., decrease in severity, incidence, and/or periodicity) compared to the amount of nausea and/or esophageal reflux observed in a patient administered omega-3 oil alone.

The methods of the invention may allow for a decrease in the dosage of one or more cardiovascular disease medications (e.g., diuretics, angiotensin-converting enzyme (ACE) inhibitors, beta blockers, blood thinning medications (e.g., aspirin), statins, and fibrates) to the subject. The methods of treating or decreasing the likelihood of developing cardiovascular disease further comprise the administration of one or more additional cardiovascular disease medications to the subject (e.g., diuretics, angiotensin-converting enzyme (ACE) inhibitors, beta blockers, blood thinning medications (e.g., aspirin), statins, and fibrates). Additional cardiovascular disease medications that may be co-administered with one or more of the provided pharmaceutical compositions are known in the art.

The methods of the invention may also decrease (e.g., by at least 5%, 10%, 15%, 20%, 25%, 30%, 35%, 40%, 45%, 50%, 55%, 60%, 70%, or 80%) the triglyceride and/or LDL cholesterol levels in a subject (e.g., compared to the triglyceride or LDL cholesterol levels in the subject prior to treatment or the triglyceride or LDL cholesterol levels in a subject or patient population not receiving treatment). For example, the methods of the invention may decrease the triglyceride levels in a subject to below 250 mg/dL (e.g., below 240 mg/dL, 230 mg/dL, 220 mg/dL, 210 mg/dL, 200 mg/dL, 190 mg/dL, 180 mg/dL, 170 mg/dL, 140 mg/dL, 130 mg/dL, 120 mg/dL, 110 mg/dL, and 100 mg/dL). In addition, the methods of the invention may decrease the LDL cholesterol levels in a subject to below 180 mg/dL (e.g., below 170 mg/dL, 160 mg/dL, and 150 mg/dL, 140 mg/dL, 130 mg/dL, 120 mg/dL, 110 mg/dL, 100 mg/dL, 90 mg/dL, 80 mg/dL, or 70 mg/dL). The methods for decreasing the triglyceride and/or LDL cholesterol levels may also result in a decrease (e.g., by at least 5%, 10%, 15%, 20%, 25%, 30%, 35%, 40%, 45%, 50%, 55%, 60%, 65%, 70%, 75%, 80%, 85%, 90%, 95%, or 100%) in nausea and/or esophageal reflux (e.g., decrease in severity, incidence, and/or periodicity) compared to the amount of nausea and/or esophageal reflux observed in a patient administered omega-3 oil alone.

The methods of the invention may allow for a decrease in the dosage of one or more (e.g., one, two, three, or four) LDL cholesterol- or triglyceride-lowering medication(s) (e.g., statins, such as atorvastatin, lovastatin, pravastatin, simvastatin, fluvastatin, and rosuvastatin) to the subject. The methods of decreasing triglyceride and/or LDL cholesterol levels may further include the administration of one or more additional LDL cholesterol- or triglyceride-lowering medications to the subject (e.g., statins, such as atorvastatin, lovastatin, pravastatin, simvastatin, fluvastatin, and rosuvastatin). Additional triglyceride- and/or LDL cholesterol-lowering medications that may be co-administered with one or more of the provided pharmaceutical compositions are known in the art.

The methods of the invention may also be used to treat or reduce (e.g., by at least 10%, 15%, 20%, 25%, 30%, 35%, 40%, 45%, 50%, 55%, 60%, 65%, 70%, 75%, 80%, 85%, 90%, 95%, or 99%) one or more (e.g., one, two, three, four, or five) symptoms of diabetes (e.g., type I diabetes, type II diabetes, and pre-diabetes) in a subject. For example, the methods of the invention may result in an increase (e.g., by at least 5%, 10%, 15%, 20%, 25%, 30%, 35%, 40%, 45%, 50%, 55%, 60%, 70%, 80%, 90%, or 95%) in insulin absorption and/or insulin sensitivity, a decrease (e.g., by at least 5%, 10%, 15%, 20%, 25%, 30%, 35%, 40%, 45%, 50%, 55%, or 60%) in blood glucose levels in a subject or patient population having elevated blood glucose (e.g., one or more blood glucose reading(s) greater than 104 mg/dL), and a decrease (e.g., by at least 5%, 10%, 15%, 20%, 25%, or 30%) in glycated hemoglobin levels in a subject or patient population having increased glycated hemoglobin levels (e.g., $HbA_{1C}$ greater than 7.0%). The methods of the invention may also result in an increase (e.g., at least 5%, 10%, 15%, 20%, 25%, 30%, 35%, 40%, 45%, 50%, 55%, or 60%) in the HDL cholesterol levels in a subject compared to the HDL cholesterol levels in the subject prior to treatment or the HDL cholesterol levels in a subject or patient population not receiving treatment. In one example of these methods of treating or reducing the severity of one or more symptoms of diabetes, the subject is administered one or more pharmaceutical compositions of the invention containing phosphatidylinositol and phosphatidic acid.

The methods of the invention may allow for a decrease in the dosage of one or more diabetes medications (e.g., insulin (e.g., lys-pro or short-acting insulin, intermediate-acting insulin, or long-acting insulin), sulfonylureas, biguanides, alpha-glycosidase inhibitors, thiazolidinediones, and meglitinides) to the subject. The methods of treating diabetes may further include the administration of one or more diabetes medications to the subject (e.g., insulin (e.g., lys-pro or short-acting insulin, intermediate-acting insulin, or long-acting insulin), sulfonylureas, biguanides, alpha-glycosidase inhibitors, thiazolidinediones, and meglitinides). Additional diabetes medications that may be co-administered with one or more of the provided pharmaceutical compositions are known in the art.

The methods of the invention may also be used to decrease (e.g., by at least 5%, 10%, 15%, 20%, 25%, 30%, 35%, 40%, 45%, 50%, 55%, 60%, 65%, 70%, 75%, 80%, 85%, 90%, 95%, or 99%) pain (e.g., acute pain or chronic pain) in a subject. For example, the methods of the invention may result in a decrease (e.g., by at least 5%, 10%, 15%, 20%, 25%, 30%, 35%, 40%, 45%, 50%, 55%, 60%, 70%, 80%, 90%, or 95%) in the pain score in one or more pain score tests (e.g., Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnaire, Wong-Baker FACES Pain Rating Scale, and Visual Analog Scale (VAS)). The methods of the invention may also result in a decrease (e.g., by at least 5%, 10%, 15%, 20%, 25%, 30%, 35%, 40%, 45%, 50%, 55%, 60%, 65%, 70%, 75%, 80%, 85%, 90%, or 95%) in the number of gastric lesions in a subject compared to the number of gastric lesions observed when an NSAID and/or a DMARD are administered alone. In one example of the methods for decreasing pain, the subject is administered one or more pharmaceutical compositions of the invention containing rosemary oil and glucosamine.

The methods of the invention may allow for a decrease in the dosage of one or more anti inflammatory/analgesics (e.g., diclofenac, diflusinal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, tramadol, acetaminophen, and aspirin) administered to the subject. The methods of decreasing pain may further include the administration of one or more (e.g., one, two, three, or four) analgesics to the subject (e.g., diclofenac, diflusinal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, tramadol, acetaminophen, and aspirin). Additional analgesics that may be co-administered with one or more of the provided pharmaceutical compositions are known in the art.

The methods of the invention may also be used to decrease (e.g., by at least 10%, 15%, 20%, 25%, 30%, 35%, 40%, 45%, 50%, 55%, 60%, 65%, 70%, 75%, 80%, 85%, 90%, 95%, or 99%) inflammation or one or more (e.g., one, two, three, four, or five) symptoms of inflammation in a subject. For example, the methods of the invention may result in a decrease (e.g., by at least 5%, 10%, 15%, 20%, 25%, 30%, 35%, 40%, 45%, 50%, 55%, 60%, 70%, 80%, 90%, or 95%) in COX-1 and/or COX-2 activity relative to the COX-1 and/or COX-2 activity in the subject prior to treatment or the COX-1 and/or COX-2 activity in a subject or patient population not receiving treatment. The methods of the invention may also result in a decrease (e.g., by at least 5%, 10%, 15%, 20%, 25%, 30%, 35%, 40%, 45%, 50%, 55%, 60%, 70%, 80%, 90%, or 95%) in white blood cell count relative the white blood cell count in the subject prior to treatment or the white blood cell count in a subject or a patient population not receiving treatment. The methods of the invention may also result in a decrease (e.g., by at least 5%, 10%, 15%, 20%, 25%, 30%, 35%, 40%, 45%, 50%, 55%, 60%, 70%, 80%, 90%, or 95%) in C-reactive protein, interleukin-6, and/or TNF-alpha levels, swelling, and/or pain in a subject relative to the amount of C-reactive protein levels, swelling, and/or pain observed in the subject prior to treatment or the amount of C-reactive protein levels, swelling, and/or pain observed in a subject or a patient population not receiving treatment. The methods of treatment may also result in a decrease (e.g., by at least 5%, 10%, 15%, 20%, 25%, 30%, 35%, 40%, 45%, 50%, 55%, 60%, 70%, 80%, 90%, or 95%) in erythrocyte sedimentation rate in a subject compared to the erythrocyte sedimentation rate in the subject prior to treatment or the erythrocyte sedimentation rate in a subject or a patient population not receiving treatment. The provided methods may also result in a decrease (e.g., by at least 5%, 10%, 15%, 20%, 25%, 30%, 35%, 40%, 45%, 50%, 55%, 60%, 65%, 70%, 75%, 80%, 85%, 90%, or 95%) in the number of gastric lesions in a subject compared to the number of gastric lesions observed when an NSAID and/or a DMARD are administered alone. In one example of the methods for decreasing inflammation, the subject is administered one or more pharmaceutical compositions of the invention containing rosemary oil or glucosamine.

The provided methods may allow for a decrease in dosage of anti-histamine used in the treatment of allergies and general inflammatory conditions. Decreasing the dosage of antihistamine will decrease one or more of the side effects of the antihistamine class (e.g., sedation).

The provided methods may also allow for a decrease in the dosage of one or more anti-inflammatory medications (e.g., NSAIDs) administered to a subject. The methods for decreasing inflammation may further include the administration of one or more (e.g., one, two, three, or four) anti-inflammatory medications to the subject (e.g., one or more NSAIDs). Additional anti-inflammatory medications that may be co-administered with one or more of the provided pharmaceutical compositions are known in the art.

The method of the invention may also be used to treat chronic pulmonary disease (e.g., asthma and chronic obstructive pulmonary disease) and irritable bowel syndrome, or reduce one or more symptoms of an autoimmune disease (e.g., multiple sclerosis and lupus erythematosus) in a subject. For example, the methods may affect at least a 10% (e.g., at least 15%, 20%, 25%, 30%, 35%, 40%, 45%, 50%, 55%, 60%, 65%, 70%, 75%, 80%, 85%, 90%, or 95%) decrease in one or more (e.g., two, three, or four) symptoms of a chronic pulmonary disease. Non-limiting examples of such symptoms include lung inflammation, pain, reduced lung capacity, and bronchioalveolar constriction. The methods may affect at least a 10% (e.g., at least 15%, 20%, 25%, 30%, 35%, 40%, 45%, 50%, 55%, 60%, 65%, 70%, 75%, 80%, 85%, 90%, or 95%) decrease in one or more (e.g., two, three, or four) symptoms of a irritable bowel syndrome or an autoimmune disease (e.g., asthma and lupus erythematosus). Non-limiting examples of symptoms of irritable bowel syndrome include intestinal pain or discomfort, intestinal inflammation or lesions, and diarrhea. Non-limiting examples of symptoms of autoimmune disease include pain (e.g., joint pain), inflammation, and loss of motor function.

The effectiveness of all the above methods of treatment may be measured by a physician using methods known in the art. In the above methods, one or more pharmaceutical compositions of the invention may be administered co-extensively (overlapping bioactive periods) or non-extensively (non-overlapping bioactive periods). The combined amount of EPA and DHA present in a single dose of the provided pharmaceutical agents may be at least 2.5 g (e.g., at least 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 5.1 g, 5.2 g, 5.3 g, 5.4 g, 5.5 g, 5.6 g, 5.7 g, 5.8 g, 5.9 g, or 6.0 g) in a volume of at least 5.0 mL (e.g., at least 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL). In these methods, the one or more pharmaceutical compositions may be administered with one or more (e.g., one, two, three, four, or five) additional therapeutic agents including, but not limited to, one or more (e.g., one, two, three, four, or five) NSAID(s), one or more (e.g., one, two, three, four, or five) DMARDS(s), one or more (e.g., one, two, three, four, or five) analgesics, one or more (e.g., one, two, three, four, or five) triglyceride- or LDL cholesterol-lowering agents (e.g., statins), one or more (e.g., one, two, three, four, or five) cardiovascular disease medications (e.g., diuretics, angiotensin-converting enzyme (ACE) inhibitors, beta blockers, blood thinning medications (e.g., aspirin), statins, and fibrates), or one or more (e.g., one, two, three, four, or five) diabetes medications (e.g., insulin (e.g., lys-pro or short-acting insulin, intermediate-acting insulin, or long-acting insulin), sulfonylureas, biguanides, alpha-glycosidase inhibitors, thiazolidinediones, and meglitinides). The one or more additional therapeutic agents may be co-administered with the one or more pharmaceutical compositions provided by the invention (e.g., in the same or separate dosage forms). In additional examples of the provided methods, the one or more additional therapeutic agents are administered following the administration of the one or more provided pharmaceutical compositions to the subject (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In additional examples of the methods, the one or more pharmaceutical compositions provided by the invention may be administered following the administration of the one or more additional therapeutic agent(s) to the subject (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In these methods, the one or more pharmaceutical compositions and the one or more additional therapeutic agents may be administered co-extensively (overlapping bioactive periods) or non-extensively (non-overlapping bioactive periods).

The amount of one or more pharmaceutical compositions that may be administered to a subject per dose may be between 0.1 mg and 6 g, 0.1 mg and 5 g, 0.1 mg and 4.5 g, 0.1 mg and 5.0 g, 100 mg and 5.0 g, 500 mg and 5.0 g, 1.0 g and 5.0 g, 2.0 g and 5.0 g, 3.0 g and 4.5 g, and 3.0 g and 4.0 g. The amount of the one or more therapeutic organic molecules that may be administered to a subject per dose may be between 0.1 mg and 2.0 g (e.g., between 0.1 mg and 1.5 mg, 0.1 mg and 1 g, 0.1 mg and 750 mg, 1 mg and 650 mg, 1 mg and 550 mg, 1 mg and 500 mg, 10 mg and 450 mg, 10 mg and 400 mg, 10 mg and 350 mg, 10 mg and 350 mg, and 10 mg and 250 mg). The amount of one or more additional therapeutic agents that may be co-administered to a subject may be between 0.1 mg and 2.0 g (e.g., between 0.1 mg and 1.5 mg, 0.1 mg and 1 g, 0.1 mg and 750 mg, 1 mg and 650 mg, 1 mg and 550 mg, 1 mg and 500 mg, 10 mg and 450 mg, 10 mg and 400 mg, 10 mg and 350 mg, 10 mg and 350 mg, and 10 mg and 250 mg).

The one or more pharmaceutical compositions provided by the invention and the one or more additional therapeutic agents may be administered to a subject once a day, twice a day, three times a day, four times a day, once a week, twice a week, three times a week, four times a week, five times a week, six times a week, seven times a week, bi-weekly, tri-weekly, or monthly. For example, the one or more pharmaceutical compositions and the one or more additional therapeutic agents may be orally administered to a subject once, twice, three times, or four times a day. The one or more pharmaceutical compositions and the one or more additional therapeutic agents may be administered via the same route of administration (e.g., oral administration) or via different routes of administration (e.g., oral and parenteral administration). The one or more pharmaceutical compositions and the one or more additional therapeutic agents may be formulated for any known route of administration, including oral, intravenous, intraarterial, intraocular, intranasal, intramuscular, and subcutaneous administration. The therapeutically effective dose of the one or more pharmaceutical compositions and the one or more additional therapeutic agents may be determined by a skilled physician using methods known in the art.

EXAMPLES

The features and other details of the invention will now be more particularly described and pointed out in the following examples describing preferred techniques and experimental results. These examples are provided for the purpose of illustrating the invention and should not be construed as limiting.

Example 1. Pharmaceutical Compositions Containing Omega-3 Oil

In order to increase the absorption efficiency of omega-3 oils in mammals (e.g., humans), a series of omega-3 compositions containing one or more adsorption enhancers were developed. An example of a pharmaceutical composition containing omega-3 oil with an increased absorption rate is shown below.

Formula I:

| Component | Weight Percentage |
| --- | --- |
| Natural Fish Oil (25% to 38% combined EPA and DHA) | 75% |
| Coconut Oil (medium chain triglyceride mix) | 5% |
| Polytocopherol (source of vitamin E) | 1% |
| Absolute Ethanol | 5% |
| Span 20, NF | 4% |
| Cremaphor ELO, NF | 10% |

An example of a pharmaceutical composition containing omega-3 oil and an additional therapeutic organic molecule is shown below.

Formula II:

| Component | Weight Percentage |
| --- | --- |
| Natural Fish Oil (25% to 38% combined EPA and DHA) | 70% |
| Coconut Oil (medium chain triglyceride mix) | 5% |
| Polytocopherol (source of vitamin E) | 1% |
| Absolute Ethanol | 5% |
| Span 20, NF | 4% |
| Cremaphor ELO, NF | 5% |
| One or more therapeutic organic molecule(s) | 10% |

In the above formulas, the natural fish oil used as a source of omega-3 oil may be a high grade omega-3 oil (e.g., OmegaMaine omega-3 oil).

The above compositions may also include one or more (e.g., one, two, three, four, or five) nitric oxide-stimulating or -releasing agent(s). The addition of one or more nitric oxide-stimulating or -releasing agent(s) may increase the blood flow in the omental arterial blood supply and help to facilitate the rapid transfer of omega-3 fatty acids and/or the one or more additional therapeutic organic molecules to the plasma.

Example 2. The Provided Omega-3 Oil-Containing Pharmaceutical Compositions Demonstrate an Increased Rate of Absorption in Humans Experiments were performed to determine the absorption rate of one of the pharmaceutical compositions provided herein (Formula I shown in Example 1). Six human volunteers were treated once a day for one month with a natural source of omega-3 oils containing 3.5 grams of EPA and DHA combined in a 10 mL dose (Group I). Eight human volunteers (Group 2) were treated once a day for one month with the composition of Formula I (shown above). For both groups, the starting omega-3 fatty acid content in whole blood was between 0.6% and 1.1% (baseline of 0.8% for EPA and DHA in red blood cell fatty acids) (Table 1).

After one month of dosing on a daily basis, the omega-3 oil fatty acid content of EPA and DHA was measured in each volunteer (Table 1). These data demonstrate that the absorption enhancers in Formula I result in a 1.8-fold increase in the absorption of EPA and DHA in humans.

TABLE 1

| Treatment | % of EPA and DHA in White Blood Cell Fatty Acids |
|---|---|
| Baseline | 0.8% |
| Group I | 3.8% |
| Group II | 6.8% |

Example 3. Analyses of the Absorption Rate of Pharmaceutical Compositions Containing Omega-3 Oil and an Additional Therapeutic Organic Molecule Additional experiments to test the absorption rate of the different omega-3 oil-containing pharmaceutical compositions described herein was illustrated in a mouse model. In these experiments, mice (4/group) were administered 25 mg/kg ibuprofen in the composition of Formula II, in 100% natural fish oil, or in saline. The time to reach $C_{max}$ and $T_{max}$ for ibuprofen was determined from mouse tail vein samples (Table 2).

The data for this experiment show that natural fish oil is an absorption enhancer and that a further increase in absorption rate and $C_{max}$ is achieved when one or more additional absorption enhancers are used (e.g., the additional absorption enhancers in Formula II).

TABLE 2

|  | Cmax | $T_{1/2}$ |
|---|---|---|
| Ibuprofen in saline | 10 µg/mL | 60 min |
| Ibuprofen in omega 3/Formula 2 | 14 µg/mL | 35 min |

Example 4. The Provided Pharmaceutical Compositions Containing Omega-3 Oil and Ketoprofen Demonstrate Reduced Formation of Stomach Lesions in Mice A negative side effect of the administration of NSAIDs in humans is the formation of stomach lesions. Pharmaceutical compositions containing omega-3 oils and ketoprofen (described herein) were tested for their ability to induce gastric lesions in a mouse model. In these experiments, fasted mice were given 10 mg/kg ketoprofen. The ketoprofen was administered in saline or in 100% fish oil. In a control experiment, mice were treated with natural omega-3 oil one-hour prior to ketoprofen administration. One-hour after ketoprofen administration, the mice were sacrificed and their stomachs analyzed for lesions (Table 3).

TABLE 3

| Treatment | Average Lesions Score/Stomach |
|---|---|
| Ketoprofen in Saline (n = 8) | 33 |
| Natural Omega-3 Oil Pretreatment (n = 8) | 8 |
| Ketoprofen in 100% Fish Oil (n = 8) | 12 |

These data show that the administration of ketoprofen in one of the pharmaceutical compositions provided by the invention (100% fish oil) results in decreased formation of stomach lesions.

Example 5. Combination Therapy of Inflammation in a Mouse Model Using an Omega-3 Oil Pharmaceutical Composition Experiments were performed to determine whether the administration of ketoprofen in combination with an omega-3 oil-containing pharmaceutical composition would decrease inflammation in a mouse model (carrageenin-induced ear swelling mouse model). In these experiments, ketoprofen was administered in a dosage (2 mg/kg) that results in a 50% decrease in induced inflammation in this mouse model. Ketoprofen was administered alone or following pretreatment with omega-3 oil. The amount of inflammation was determined by measuring the ear volume of the treated mice compared to control mice not receiving ketoprofen (Table 4). Eight mice were used for each treatment.

TABLE 4

| Treatment | % of Inhibition of Inflammation |
|---|---|
| Pretreatment with Omega-3 Oil, Followed by Ketoprofen | 85% |
| Ketoprofen Only | 45% |

These data demonstrate that administration of an omega-3 oil-containing pharmaceutical composition prior to administration of ketoprofen results in an increased reduction in inflammation compared to the administration of ketoprofen alone.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. An oral composition comprising omega-3 oil in an effective amount of a non-hydrophilic absorption enhancer comprising vitamin E and medium chain triglycerides (MCTs), wherein the omega-3 oil comprises eicosapentaenoic acid (EPA) and docosahexaenoic acid (DHA), wherein the composition comprises greater than 3.0 g combined eicosapentaenoic acid (EPA) and docosahexaenoic acid (DHA) per 10 mL of said composition, wherein the composition is formulated as a multi-component clear liquid, and wherein the effective amount is determined by obtaining more than a 1.8-fold increase in the absorption of EPA and DHA.

2. The composition of claim 1, wherein said non-hydrophilic absorption enhancer is less than 30% of the composition's total mass.

3. The composition of claim 1, further comprising another oil that is a herbal-based oil in an amount of 1% to 10% of the composition's total mass.

4. The composition of claim 3, wherein the herbal-based oil is selected from the group consisting of rosemary oil, basil oil, turmeric oil, and ginger oil.

5. The composition of claim 1, wherein the amount of vitamin E present in a single dose of said composition is between 13.4 to 134 mg.

6. The composition of claim 1, wherein the amount of vitamin E present is 1.3% to 13.4% of the composition's mass.

7. The composition of claim 1, wherein said MCTs are from coconut oil.

8. The composition of claim 1, wherein said MCTs are between 1% to 10% of the composition's total mass.

9. The composition of claim 8, wherein said MCTs are 5% of the composition's total mass.

10. The composition of claim 1, further comprising another agent that is phosphatidylcholine.

11. The composition of claim 1, further comprising one or more of nitric oxide-stimulating agents, nitric oxide-releasing agents, glucosamine, ethanol, and Tween surfactant.

12. The composition of claim 1, further comprising one or more other therapeutic organic molecule(s), said one or more other therapeutic organic molecule(s) having with a molecular weight between 100 g/mole and 800 g/mole, a log P value greater than 2, or a melting point below 200° C.

13. The composition of claim 12, wherein said one or more other therapeutic organic molecule(s) is a non-steroidal anti-inflammatory drug (NSAID), a disease-modifying anti-rheumatic drug (DMARD), fenofibrate, a statin, niacin, or an H-1 antihistamine.

14. The composition of claim 13, wherein a dose of said composition contains 5 mg/mL to 20 mg/mL of fenofibrate.

15. The composition of claim 13, wherein a dose of said composition contains 1 mg/mL to 4 mg/mL of a statin.

16. The composition of claim 13, wherein said one or more other therapeutic organic molecule(s) is a NSAID selected from the group consisting of ketoprofen, ibuprofen, diflunisal, diclofenac, and naproxen.

17. The composition of claim 13, wherein said one or more other therapeutic organic molecule(s) is DMARD that is methotrexate.

18. The composition of claim 13, wherein said one or more other therapeutic organic molecule(s) is an H-1 antihistamine selected from the group consisting of imipramine, doxepin, diphenhydramine, and triprolidine.

19. The composition of claim 1, further comprising one or more additional agents selected from the group consisting of: phosphatidylserine, phosphatidylethanolamine, phosphatidylinositol, and phosphatidic acid.

20. A kit comprising:
(i) the composition of claim 1; and
(ii) instructions for administering said composition to a subject.

21. A method of decreasing a cardiovascular disease in a subject in need thereof by administering to said subject the composition of claim 1 in an amount sufficient to reduce triglyceride and/or low-density lipoprotein (LDL) cholesterol levels in the blood of said subject, or to increase the amount of omega-3 oil present in the cell membranes of red blood cells in said subject.

22. A method of decreasing the triglyceride and/or low-density lipoprotein (LDL) cholesterol levels in a subject in need thereof comprising administering the composition of claim 1 to said subject.

23. A method of treating diabetes in a subject in need thereof comprising administering to said subject a composition of claim 1 in an amount sufficient to increase insulin sensitivity in said subject or increase high-density lipoprotein (HDL) cholesterol level in the blood of said subject.

24. A method of decreasing pain or inflammation in a subject in need thereof comprising administering to said subject the composition of claim 1.

25. A method of treating a chronic pulmonary disease or irritable bowel syndrome, or reducing one or more symptoms of an autoimmune disease in a subject in need thereof comprising administering to said subject a composition of claim 1.

26. A method of formulating an oral omega-3 oil-containing pharmaceutical composition, comprising the step of combining a fish omega-3 oil with an effective amount of an absorption enhancer comprising one or more solvents or agents selected from the group consisting of: a herbal-based oil, vitamin E, medium chain triglycerides, lecithin, phosphatidylcholine, glucosamine, ethanol, a Tween surfactant, phosphatidylserine, phosphatidylethanolamine, phosphatidylinositol, phosphatidic acid, coconut oil, polytocopherol, sorbitan laurate, cremaphor (polyethoxylated castor oil), an amide of an intermediate (C-6 to C-12) chain fatty acid, an amide of a long chain (C-12 to C-24 fatty acid), lauric alcohol, and lauric acid, wherein the effective amount is determined by obtaining greater than a 1.8-fold increase in the absorption of omega-3 eicosapentaenoic acid (EPA) and docosahexaenoic acid (DHA).

27. A method of formulating an oral pharmaceutical composition containing omega-3 oil and one or more other therapeutic organic molecule(s), comprising the step of combining a fish omega-3 oil and one or more other therapeutic organic molecule(s) with an effective amount of an absorption enhancer comprising one or more solvents or agents selected from the group consisting of: a herbal-based oil, vitamin E, medium chain triglycerides (MCTs), lecithin, phosphatidylcholine, glucosamine, ethanol, a Tween surfactant, phosphatidylserine, phosphatidylethanolamine, phosphatidylinositol, phosphatidic acid, coconut oil, polytocopherol, sorbitan laurate, cremaphor (polyethoxylated castor oil), an amide of an intermediate (C-6 to C-12) chain fatty acid, an amide of a long chain (C-12 to C-24 fatty acid), lauric alcohol, and lauric acid, wherein the effective amount is determined by obtaining greater than a 1.8-fold increase in the absorption of omega-3 eicosapentaenoic acid (EPA) and docosahexaenoic acid (DHA).

28. The composition of claim 1, wherein said composition comprises at least 25% w/w of omega-3 oil and 1% to 10% w/w of MCTs.

29. The composition of claim 1, wherein said composition comprises:
70% to 80% w/w of natural fish oil as a source of said omega-3 oil; 5% to 15% w/w of coconut oil as a source of said medium chain triglycerides; 0.5% to 5% w/w polytocopherol as a source of said vitamin E; 1% to 10% w/w absolute ethanol; 1% to 10% w/w sorbitan laurate; and 1% to 10% w/w cremaphor (polyethoxylated castor oil); or
70% to 80% w/w of natural fish oil as a source of said omega-3 oil: 5% to 15% w/w coconut oil as a source of said medium chain triglycerides; 0.5% to 5% w/w polytocopherol as a source of said vitamin E; 1% to 5% w/w absolute ethanol; and 5% to 15% w/w cremaphor (polyethoxylated castor oil); or
65% to 75% w/w of natural fish oil as a source of said omega-3 oil; 1% to 10% w/w of coconut oil as a source of said medium chain triglycerides; 0.5% to 5% w/w polytocopherol as a source of said vitamin E; 1% to 10% w/w absolute ethanol; 1% to 10% w/w sorbitan laurate; 1% to 10% w/w cremaphor (polyethoxylated castor oil); and 1% to 10% w/w of one or more other therapeutic organic molecule(s); or
65% to 75% w/w of natural fish oil as a source of said omega-3 oil; 1% to 10% w/w of coconut oil as a source of said medium chain triglycerides; 0.5% to 5% w/w polytocopherol as a source of said vitamin E; 1% to 5% w/w absolute ethanol; 1% to 10% w/w sorbitan laurate;

1% to 15% w/w cremaphor (polyethoxylated castor oil); and 1% to 10% w/w of one or more therapeutic organic molecule(s).

\* \* \* \* \*